(12) United States Patent
Cheong et al.

(10) Patent No.: US 9,101,610 B2
(45) Date of Patent: Aug. 11, 2015

(54) ANTI C-MET HUMANIZED ANTIBODY AND USES THEREOF

(75) Inventors: Kwang Ho Cheong, Seoul (KR); Seunghyun Lee, Suwon-si (KR); Geun Woong Kim, Yongin-si (KR); Kyung-Ah Kim, Seongnam-si (KR); Young Mi Oh, Seoul (KR); Saet Byoul Lee, Seoul (KR); Soo-yeon Jung, Seongnam-si (KR); Yunju Jeong, Anyang-si (KR); Young Kue Han, Daejeon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 134 days.

(21) Appl. No.: 13/589,789

(22) Filed: Aug. 20, 2012

(65) Prior Publication Data

US 2013/0089556 A1    Apr. 11, 2013

(30) Foreign Application Priority Data

Oct. 5, 2011    (KR) .................. 10-2011-0101291

(51) Int. Cl.
| | | |
|---|---|---|
| *A61K 39/395* | (2006.01) | |
| *A61P 35/00* | (2006.01) | |
| *C07K 16/30* | (2006.01) | |
| *C07K 16/28* | (2006.01) | |
| *A61K 39/00* | (2006.01) | |

(52) U.S. Cl.
CPC ....... *A61K 39/39558* (2013.01); *C07K 16/2863* (2013.01); *A61K 2039/505* (2013.01); *C07K 2317/24* (2013.01); *C07K 2317/53* (2013.01); *C07K 2317/565* (2013.01); *C07K 2317/73* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,892,550 B2 | 2/2011 | Dennis et al. |
| 2011/0097262 A1 | 4/2011 | Goetsch et al. |
| 2011/0104176 A1* | 5/2011 | Cheong et al. ............ 424/152.1 |

FOREIGN PATENT DOCUMENTS

| | | | |
|---|---|---|---|
| EP | 2316484 | * | 5/2011 |
| KR | 1020110047698 A | | 9/2011 |
| WO | WO 2010/064089 A1 | | 6/2010 |
| WO | WO 2010/069765 A1 | | 6/2010 |

OTHER PUBLICATIONS

Portolano, The Journal of Immunology, vol. 150, No. 3, p. 880-887, 1993.*
Paul, Fundamental Immunology: Third Edition, p. 292-295, 1993.*

* cited by examiner

*Primary Examiner* — Mark Halvorson
*Assistant Examiner* — Michael D Allen
(74) *Attorney, Agent, or Firm* — Leydig, Voit & Mayer, Ltd.

(57) ABSTRACT

An anti c-Met antibody, a composition comprising the antibody, and a method for preventing or treating cancer by administering the composition is provided.

16 Claims, 9 Drawing Sheets

SEQUENCE LISTING

```
<160> NUMBER OF SEQ ID NOS: 37

<210> SEQ ID NO 1
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: heavy chain variable region of anti c-Met
      humanized antibody(huAbF46-H1)

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115
```

```
<210> SEQ ID NO 2
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: light chain variable region of anti c-Met
      humanized antibody(huAbF46-H1)

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 3
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: heavy chain variable region of anti c-Met
      humanized antibody(huAbF46-H4)
<220> FEATURE:
<221> NAME/KEY: MISC_FEATURE
<223> OTHER INFORMATION: heavy chain variable region of anti c-Met
      humanized antibody(huAbF46-H4)

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115
```

```
<210> SEQ ID NO 4
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: light chain variable region of anti c-Met
      humanized antibody(huAbF46-H4)

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 5
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: modified hinge region(U7-HC6)

<400> SEQUENCE: 5

Glu Pro Ser Cys Asp Lys His Cys Cys Pro Pro Cys Pro
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: modified hinge region(U6-HC7)

<400> SEQUENCE: 6

Glu Pro Lys Ser Cys Asp Cys His Cys Pro Pro Cys Pro
1               5                   10

<210> SEQ ID NO 7
<211> LENGTH: 1416
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of heavy chain of chAbF46
```

```
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 7
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg gttttattta gaaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata ctggtttgc ttactgggc aagggactc tggtcactgt ctctgcagct        420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc cccatcccg ggaggagatg     1140 accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 8
<211> LENGTH: 759
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of light chain of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(90)
<223> OTHER INFORMATION: signal sequence
<220> FEATURE:
<221> NAME/KEY: misc_feature
<222> LOCATION: (91)..(432)
<223> OTHER INFORMATION: VL - light chain variable region
<220> FEATURE:
<221> NAME/KEY: misc_feature
<222> LOCATION: (430)..(435)
<223> OTHER INFORMATION: BsiWI restriction site
<220> FEATURE:
<221> NAME/KEY: misc_feature
<222> LOCATION: (433)..(750)
<223> OTHER INFORMATION: CL - light chain constant region
<220> FEATURE:
<221> NAME/KEY: misc_feature
<222> LOCATION: (751)..(753)
<223> OTHER INFORMATION: stop codon
<220> FEATURE:
<221> NAME/KEY: misc_feature
<222> LOCATION: (754)..(759)
<223> OTHER INFORMATION: XhoI restriction site

<400> SEQUENCE: 8

```
gaattcacta gtgattaatt cgccgccacc atgattcac aggcccaggt cctcatgttg      60
ctgctgctat cggtatctgg tacctgtgga cattttga tgacccagtc tccatcctcc     120
ctgactgtgt cagcaggaga aaggtcact atgagctgca agtccagtca gagtctttta     180
gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct tcccgccatc tgatgagcag     480
ttgaaatctg gaactgcctc tgttgtgtgc ctgctgaata acttctatcc cagagaggcc     540
aaagtacagt ggaaggtgga taacgccctc caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                          759
```

<210> SEQ ID NO 9
<211> LENGTH: 447
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H1-heavy

<400> SEQUENCE: 9

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445
```

<210> SEQ ID NO 10
<211> LENGTH: 447
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H3-heavy

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 11
<211> LENGTH: 447
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H4-heavy

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220
```

```
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 12
<211> LENGTH: 220
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H1-light

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125
```

```
Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 13
<211> LENGTH: 220
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H2-light

<400> SEQUENCE: 13

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 14
<211> LENGTH: 220
<212> TYPE: PRT
<213> ORGANISM: Artificial Sequence
<220> FEATURE:
```

<223> OTHER INFORMATION: Synthetic
<220> FEATURE:
<221> NAME/KEY: MISC_FEATURE
<223> OTHER INFORMATION: amino acid sequence of H3-light

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 15
<211> LENGTH: 219
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of H4-light

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 16
<211> LENGTH: 1350
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H1-heavy

<400> SEQUENCE: 16
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg gctggagtg gttgggcttt attagaaaca agctaacgg ttacaccaca      180 gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt tgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660 gacaaaactc acacatgccc accgtgccca gcacctgaac tcctggggg accgtcagtc      720 ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc ccatcgaga aaaccatctc aaagccaaa     1020 gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260

```
aacgtcttct catgctccgt gatgcatgag gctctgcaca accactacac gcagaagagc    1320 ctctcccgt ctccgggtaa atgactcgag                                      1350
```

<210> SEQ ID NO 17
<211> LENGTH: 1350
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H3-heavy

<400> SEQUENCE: 17

```
gaggtgcagc tggtggagtc tgggggaggc ttggtccagc ctggagggtc cctgagactc     60
tcctgtgcag cctctggatt caccttcact gactactaca tgagctgggt ccgccaggct    120
ccagggaagg gctggagtg gttgggcttt attagaaaca agctaacgg ttacaccaca      180
gaatacagtg cgtctgtgaa aggcagattc accatctcaa gagataattc aaagaactca    240
ctgtatctgc aaatgaacag cctgcgtgct gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gacaaaactc acacatgccc accgtgccca gcacctgaac tcctgggggg accgtcagtc    720
ttcctcttcc cccccaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga tgaccaag    1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctcccctgt ctccgggtaa atgactcgag                                    1350
```

<210> SEQ ID NO 18
<211> LENGTH: 1350
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H4-heavy

<400> SEQUENCE: 18

```
gaggttcagc tggtggagtc tggcggtggc ctggtgcagc caggggggctc actccgtttg    60
```

| | |
|---|---|
| tcctgtgcag cttctggctt caccttcact gattactaca tgagctgggt gcgtcaggcc | 120 |
| ccgggtaagg gcctggaatg gttgggtttt attagaaaca aagctaatgg ttacacaaca | 180 |
| gagtacagtg catctgtgaa gggtcgtttc actataagca gagataattc aaaaacaca | 240 |
| ctgtacctgc agatgaacag cctgcgtgct gaggacactg ccgtctatta ttgtgctaga | 300 |
| gataactggt ttgcttactg gggccaaggg actctggtca ccgtctcctc ggctagcacc | 360 |
| aagggcccat cggtcttccc cctggcaccc tcctccaaga gcacctctgg ggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaaa ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga tgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca gagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 19
<211> LENGTH: 669
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H1-light

<400> SEQUENCE: 19

| | |
|---|---|
| gacatcgtga tgacccagtc tccagactcc ctggctgtgt ctctgggcga gagggccacc | 60 |
| atcaactgca gtccagcca gagtcttta gctagcggca accaaaataa ctacttagct | 120 |
| tggcaccagc agaaaccagg acagcctcct aagatgctca tatttgggc atctacccgg | 180 |
| gtatccgggg tccctgaccg attcagtggc agcgggtctg ggacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |

```
tgactcgag                                                              669

<210> SEQ ID NO 20
<211> LENGTH: 669
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H2-light

<400> SEQUENCE: 20
gatattgtga tgacccagac tccactctcc ctgcccgtca ccctggaga gccggcctcc        60 atctcctgca agtccagtca gagtctttta gctagtggca accaaaataa ctacttggcc      120
tggcacctgc agaagccagg gcagtctcca cagatgctga tcatttgggc atccactagg      180
gtatctggag tcccagacag gttcagtggc agtgggtcag gcactgattt cacactgaaa      240
atcagcaggg tggaggctga ggatgttgga gtttattact gccagcagtc ctacagcgct      300
ccgctcacgt tcggacaggg taccaagctg gagctcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
tgactcgag                                                              669

<210> SEQ ID NO 21
<211> LENGTH: 669
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H3-light

<400> SEQUENCE: 21
gacatcgtga tgacccagtc tccagactcc ctggctgtgt ctctgggcga gagggccacc       60
atcaactgca agtccagcca gagtctttta gctagcggca accaaaataa ctacttagct      120
tggtaccagc agaaaccagg acagcctcct aagctgctca ttatttgggc atctacccgg      180
gtatccgggg tccctgaccg attcagtggc agcgggtctg ggacagattt cactctcacc      240
atcagcagcc tgcaggctga agatgtggca gtttattact gtcagcaatc ctatagtgct      300
cctctcacgt tcggaggcgg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
tgactcgag                                                              669

<210> SEQ ID NO 22
<211> LENGTH: 669
```

-continued

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of H4-light
<220> FEATURE:
<221> NAME/KEY: misc_feature
<223> OTHER INFORMATION: nucleotide sequence of H4-light

<400> SEQUENCE: 22
gatatccaga tgacccagtc cccgagctcc ctgtccgcct ctgtgggcga tagggtcacc    60
atcacctgca gtccagtca gagtctttta gctagtggca accaaaataa ctacttggcc   120
tggcaccaac agaaaccagg aaaagctccg aaaatgctga ttatttgggc atccactagg   180
gtatctggag tccttctcg cttctctgga tccgggtctg ggacggattt cactctgacc   240
atcagcagtc tgcagccgga agacttcgca acttattact gtcagcagtc ctacagcgct   300
ccgctcacgt tcggacaggg taccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                          669

<210> SEQ ID NO 23
<211> LENGTH: 15
<212> TYPE: PRT
<213> ORGANISM: Homo sapiens

<400> SEQUENCE: 23

Glu Pro Lys Ser Cys Asp Lys Thr His Thr Cys Pro Pro Cys Pro
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: modified hinge region(U3-HC9)

<400> SEQUENCE: 24

Glu Arg Lys Cys Cys Val Glu Cys Pro Pro Cys Pro
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: modified hinge region(U6-HC8)

<400> SEQUENCE: 25

Glu Pro Arg Asp Cys Gly Cys Lys Pro Cys Pro Pro Cys Pro
1               5                   10
```

```
<210> SEQ ID NO 26
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: modified hinge region(U8-HC5)

<400> SEQUENCE: 26

Glu Lys Cys Asp Lys Thr His Thr Cys Pro Pro Cys Pro
1               5                   10

<210> SEQ ID NO 27
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of modified hinge region
      (U7-HC6)

<400> SEQUENCE: 27
gagcccaaaa gctgcgattg ccactgtcct ccatgtcca                           39

<210> SEQ ID NO 28
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of modified hinge region
      (U3-HC9)

<400> SEQUENCE: 28
gagaggaagt gctgtgtgga gtgccccccc tgccca                              36

<210> SEQ ID NO 29
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of modified hinge region
      (U6-HC8)

<400> SEQUENCE: 29
gagccacggg actgtggctg caagccctgc cctccgtgtc ca                       42

<210> SEQ ID NO 30
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of modified hinge region
      (U6-HC7)

<400> SEQUENCE: 30
```
gagcccaaaa gctgcgattg ccactgtcct ccatgtcca                                    39

<210> SEQ ID NO 31
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of modified hinge region
      (U8-HC5)

<400> SEQUENCE: 31
gagaaatgtg acaaaactca cacatgtcct ccatgtcca                                    39

<210> SEQ ID NO 32
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: heavy chain CDR1 of AbF46

<400> SEQUENCE: 32

Asp Tyr Tyr Met Ser
1               5

<210> SEQ ID NO 33
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: heavy chain CDR2 of AbF46

<400> SEQUENCE: 33

Phe Ile Arg Asn Lys Ala Asn Gly Tyr Thr Thr Glu Tyr Ser Ala Ser
1               5                   10                  15

Val Lys Gly

<210> SEQ ID NO 34
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: heavy chain CDR3 of AbF46

<400> SEQUENCE: 34

Asp Asn Trp Phe Ala Tyr
1               5

<210> SEQ ID NO 35
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: light chain CDR1 of AbF46

-continued

```
<400> SEQUENCE: 35

Lys Ser Ser Gln Ser Leu Leu Ala Ser Gly Asn Gln Asn Asn Tyr Leu
1               5                   10                  15

Ala

<210> SEQ ID NO 36
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: light chain CDR2 of AbF46

<400> SEQUENCE: 36

Trp Ala Ser Thr Arg Val Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: light chain CDR3 of AbF46

<400> SEQUENCE: 37

Gln Gln Ser Tyr Ser Ala Pro Leu Thr
1               5
```

ANTI C-MET HUMANIZED ANTIBODY AND USES THEREOF

CROSS-REFERENCE TO RELATED APPLICATIONS

This application claims the benefit of Korean Patent Application No. 10-2011-0101291, filed on Oct. 5, 2011, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 44,982 Byte ASCII (Text) file named "Replacement710047_ST25.txt," created on Nov. 2, 2012.

BACKGROUND c-Met is a receptor for hepatocyte growth factor (HGF). HGF is a cytokine that binds the extracellular region of the c-Met receptor tyrosine kinase to induce mitogenesis, movement, morphogenesis, and angiogenesis in various normal cells and tumor cells. c-Met is a representative receptor tyrosine kinase existing on the surface of cells, is itself a proto-oncogene, and is sometimes involved in various mechanisms related to cancer, such as cancer development, metastasis, migration, invasion, and angiogenesis, independent from a ligand (e.g., HGF). Thus, c-Met recently has been emerging as a new target for anti-cancer therapy.

In particular, c-Met is known to be involved in induction of resistance to commonly used anti-cancer drugs and, thus, is regarded as important with respect to personalized treatments. Representative anti-cancer therapeutic drugs targeting epidermal growth factor receptor (EGFR) (also known as ERBB1), such as ERBITUX™ (cetuximab) and TARCEVA™ (erlotinib), work by blocking the transduction of signals related to a cancer development mechanism. In addition, HERCEPTIN™ (trastuzumab), which is well known as a breast cancer therapeutic drug, targets ERBB2 (HER2) and works by blocking the transduction of signals necessary for cell proliferation.

Recent reports indicate that some patients are resistant to the drugs described above due to the overexpression of c-Met protein, wherein transduction of other signals that induce cell proliferation is activated. Thus, to many drug companies, c-Met has emerged as a target molecule for anti-cancer drugs.

The related art discloses antibody therapeutic drugs that inhibit the function of c-Met. However, in this related art, the antibody induces dimerization of c-Met molecules, thereby causing cancer.

In another related art, which discloses an antibody therapeutic drug inhibiting the function of c-Met, the antibody is capable of inhibiting the binding of c-Met to HGF c-Met, which is a c-Met ligand, but the binding of the antibody to c-Met induces the dimerization of c-Met, independent from the ligand. As a result, the antibody acts as an agonist that induces the transduction of cancer-causing signals.

Another related art discloses, to prevent the dimerization of c-Met, a one-armed antagonistic antibody of c-Met, which is prepared by modifying an agonist, and a two-armed antibody using a genetic recombinant method. Product development in clinical trials is currently in the pipeline. However, even in this related art, the antibody works only when the treatment is performed together with chemical therapy. When the antibody is independently treated, anti-cancer therapeutic effects are proven to be low.

Therefore, there is still a need to develop a new pharmaceutical composition for preventing and treating cancer that inhibits the function of c-Met.

SUMMARY

The invention provides an antibody comprising the amino acid sequences of SEQ ID NO: 32, SEQ ID NO: 33, SEQ ID NO: 34, SEQ ID NO: 35, SEQ ID NO: 36, and SEQ ID NO: 37, which correspond to the complementarity determining regions of the heavy and light chains, respectively, of an anti c-Met antibody. The invention also provides compositions comprising the antibody.

The invention provides a heavy chain variable region of an anti c-Met humanized antibody comprising SEQ ID NO: 1 or SEQ ID NO: 3.

The invention also provides a light chain variable region of an anti c-Met humanized antibody comprising SEQ ID NO: 2 or SEQ ID NO: 4.

The invention further provides a method for preventing or treating cancer comprising administering the inventive compositions to a subject, thereby preventing or treating cancer in a subject.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
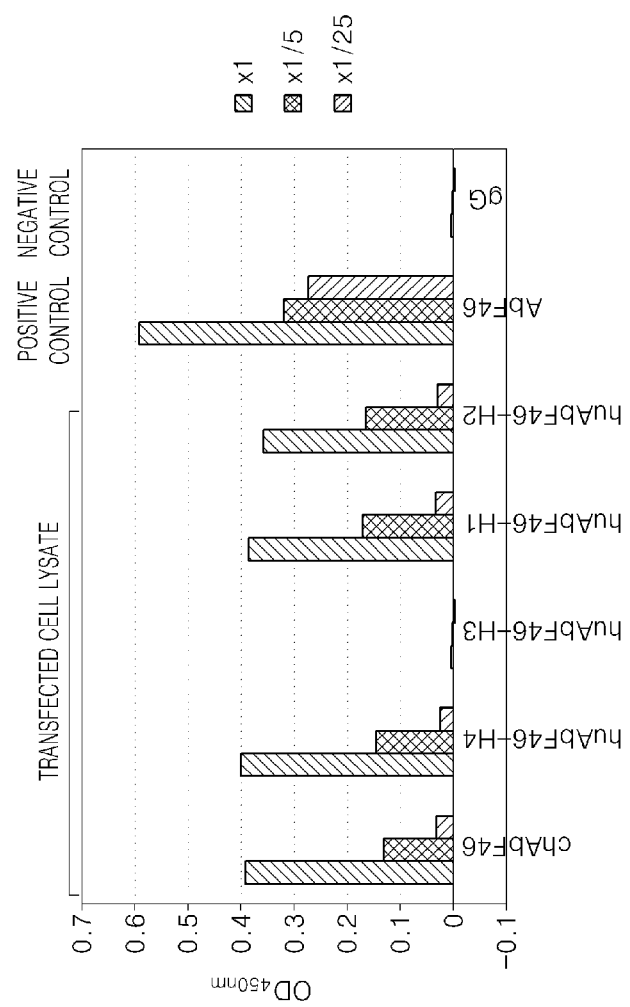
FIG. 1 is a graph illustrating the ability of the chimeric antibody chAbF46 and 3 types of humanized antibodies (huAbF46-H1, huAbF46-H2, and huAbF46-H4) to bind to c-Met protein. The optical density (OD) at 450 nM is on the y-axis and particular antibodies on the x-axis, wherein x1/5, x1/25 refer to dilution (5× dilution and 25× dilution, respectively).

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

The invention provides an antibody comprising the amino acid sequences of SEQ ID NO: 32, SEQ ID NO: 33, SEQ ID NO: 34, SEQ ID NO: 35, SEQ ID NO: 36, and SEQ ID NO: 37, which correspond to the complementarity determining regions of the heavy and light chains, respectively, of an anti c-Met antibody. Preferably, the antibody is an anti-cMet humanized antibody.

According to an aspect of the present invention, the anti c-Met humanized antibody comprises a heavy chain variable region comprising SEQ ID NO: 1 and a light chain variable region comprising SEQ ID NO: 2.

According to another aspect of the present invention, the anti c-Met humanized antibody comprises a heavy chain variable region comprising SEQ ID NO: 3 and a light chain variable region comprising SEQ ID NO 4.

The term "c-Met" or "c-Met protein" refers to a receptor tyrosine kinase that binds to hepatocyte growth factor (HGF). The c-Met protein is a polypeptide encoded by the nucleotide sequence identified as GenBank Accession Number NM_000245 or corresponding to the amino acid sequence of GenBank Accession Number NM_000236 and/or extracellular regions thereof. The receptor tyrosine kinase c-Met participates in various mechanisms, such as cancer development, metastasis, migration, invasion, and angiogenesis.

The c-Met can be any suitable c-Met, such as a mammalian C-Met (e.g., a human, monkey, mouse, or a rat c-Met).

Animal-derived antibodies produced by immunizing non-immune animals with a desired antigen generally invoke immunogenicity when injected to humans for the purpose of medical treatment, so chimeric antibodies have been developed to inhibit such immunogenicity. Chimeric antibodies are prepared by replacing constant regions of animal-derived antibodies causing an anti-isotype response with constant regions of human antibodies using genetic engineering. Chimeric antibodies are considerably improved in an anti-isotype response compared to animal-derived antibodies, but animal-derived amino acids are still present in variable regions, so chimeric antibodies can have side effects with respect to a potential anti-idiotypic response. Humanized antibodies are developed to reduce such side effects. Humanized antibodies are produced by transplanting complementarity determining regions (CDRs) in variable regions of chimeric antibodies to a human antibody framework. CDRs serve an important role in antigen binding.

The most important thing in CDR grafting to produce humanized antibodies is choosing the most optimized human antibodies for accepting the CDRs of animal-derived antibodies, and thus use of an antibody database, analysis of a crystal structure, and technology for molecule modeling are used. However, even when the CDRs of animal-derived antibodies are grafted to the most optimized human antibody framework, amino acids positioned in a framework of the animal-derived antibodies affecting antigen binding are present. Therefore, in many cases, an antigen binding force is not maintained, and thus application of additional antibody engineering technology for recovering the antigen binding force is necessary.

In another aspect, the invention provides a heavy chain variable region comprising the amino acid sequence of SEQ ID NO: 1 or SEQ ID NO: 3. Additionally, the invention provides a light chain variable region comprising the amino acid sequence of SEQ ID NO: 2 or SEQ ID NO: 4.

According to an embodiment, the antibodies may be monoclonal antibodies.

A complete antibody includes two full-length light chains and two full-length heavy chains, where each light chain is linked to the heavy chain by disulfide bonds. The antibody has a heavy chain constant region and a light chain constant region. The heavy chain constant region is of a gamma (γ), mu (μ), alpha (α), delta (δ), or epsilon (ε) type, which can be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

The term "heavy chain" refers to full-length heavy chain and fragments thereof comprising a variable region ($V_H$) that includes the CDRs (the presence of which are necessary for antigen binding), three constant region domains ($C_{H1}$, $C_{H2}$, and $C_{H3}$), and a hinge.

The term "light chain" refers to a full-length light chain and fragments thereof comprising a variable region ($V_L$) that includes the CDRs (the presence of which are necessary for antigen binding) and a constant region ($C_L$).

The term "CDRs" as used herein refers to the amino acid residues of an antibody variable domain, the presence of which is necessary for antigen binding. Specifically, they reside in hypervariable regions of a heavy chain and a light chain of immunoglobulin. Each variable domain typically has three CDRs identified as CDR1 (CDRH1 & CDRL1), CDR2 (CDRH2 & CDRL2), and CDR3 (CDRH3 & CDRL3). The CDRs provide contact residues that play a major role in the binding of antibodies to antigens or epitopes.

The term "specifically binding" or "specifically recognized" is well known to one of ordinary skill in the art, and indicates that an antibody and an antigen specifically interact with each other to lead to an immunological activity.

According to an embodiment of the present invention, the antibody can be an antigen binding fragment selected from the group consisting of scFv, (scFv)$_2$, Fab, Fab' and F(ab')$_2$.

The term "antigen binding fragment(s)" as used herein refers to fragments comprising portions of an intact antibody with antigen binding regions. For example, the antigen binding fragment can be a scFv, (scFv)$_2$, Fab, Fab', or F(ab')$_2$, but is not limited thereto. The Fab fragment contains a variable and constant domain of the light chain and a variable domain and the first constant domain ($C_{H1}$) of the heavy chain. The Fab fragment possesses one antigen binding site. The Fab' fragment is different from the Fab fragment in that Fab' has a hinge region with at least one cysteine residue at the C-terminal of $C_{H1}$. The F(ab')$_2$ fragment comprises a pair of Fab fragments, which are generally covalently linked through a disulfide bond near their carboxy termini by hinge cysteine residues between them. The Fv fragment is an antibody fragment which contains a complete antigen recognition and binding site. This region consists of a dimer of one heavy and one light chain variable domain in tight association, and a recombinant technique for producing the Fv fragment is well-known in the art. The Fv fragment has a structure in which the heavy chain and the light chain variable regions are linked by a non-covalent bond. A single-chain Fv (scFv) fragment generally has a dimer structure in which the heavy chain and the light chain variable regions are covalently bound via a peptide linker, whereas a disulfide-linked (scFv)$_2$ fragment has a structure in which two scFv fragments are directly linked to each other at the C-termini through a peptide linker. The antigen binding fragment can be obtained by any suitable manner, such as by using protease (e.g., papain to obtain Fab fragments and pepsin to obtain F(ab')$_2$ fragments). The antigen binding fragment can be prepared by any suitable techniques, such as a genetic recombinant technique.

According to an embodiment of the present invention, the antibody includes a hinge region with modified amino acid sequences, wherein one or more (e.g., 2, 3, 4, 5, 6, 7, 8, 9, 10, or more) amino acids has been deleted, inserted, or substituted. For example, the antibody can include a hinge region comprising SEQ ID NO: 5 or SEQ ID NO: 6.

The term "hinge region" refers to a region included in a heavy chain of an antibody, which is present between the $C_{H1}$ and $C_{H2}$ regions. The hinge region provides flexibility to the antigen binding site in the antibody.

When an animal-derived antibody goes through a chimerization process, an animal-derived IgG1 hinge is replaced with a human IgG1 hinge, but a length of the animal-derived IgG1 hinge is shorter than the human IgG1 hinge, and disulfide bonds between two heavy chains are reduced from 3 to 2. Thus, rigidity of the hinges may have different effects. Therefore, modification of a hinge region can increase an antigen binding efficiency of a humanized antibody. Methods to delete, insert, or substitute an amino acid (e.g., for the purpose of modifying amino acid sequences of the hinge region) are well known in the art.

According to another embodiment, the invention provides a heavy chain variable region of an anti c-Met humanized antibody comprising SEQ ID NO: 1 or SEQ ID NO: 3.

In an alternative embodiment, the invention provides a light chain variable region of an anti c-Met humanized antibody comprising SEQ ID NO: 2 or SEQ ID NO: 4.

The invention also provides compositions (e.g., pharmaceutical compositions) comprising the inventive antibodies and a pharmaceutically acceptable carrier, diluent, or excipient. The pharmaceutically acceptable carriers included in the composition can include commonly used lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition can further include a lubricant, a wetting agent, a sweetener, a flavor enhancer, an emulsifying agent, a suspension agent, and a preservative.

The compositions can be used for any suitable purpose including, but not limited to, for preventing or treating cancer and/or angiogenesis-related diseases. The cancer to be treated or prevented can any suitable cancer including, but not limited to, squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, and head and neck cancers. Therefore, the invention also provides a method of treating or preventing cancer and/or other angiogenesis-related diseases comprising administering the inventive antibodies or compositions (e.g., pharmaceutical compositions) to a patient (e.g., a mammal, such as a mouse, rat, guinea pig, rabbit, cat, dog, pig, cow, horse, primate, or human).

The inventive antibodies and compositions can be administered by any suitable method (e.g., orally or parenterally). Parenteral administration includes intravenous injection, subcutaneous injection, muscular injection, intraperitoneal injection, endothelial administration, local administration, intranasal administration, intrapulmonary administration, and rectal administration. Since oral administration can lead to digestions of protein or peptide, preferably, an active ingredient can be coated or formulated in the composition (e.g., pharmaceutical composition) to prevent digestion. In addition, the composition (e.g., pharmaceutical composition can be equipped with a moiety that allows targeting of specific cells upon administration.

Angiogenesis-related disease results when new blood vessels either grow excessively or insufficiently. In the context of the invention, angiogenesis-related disease refers to excess growth of new blood vessels, such as in cancer, diabetic blindness, age-related macular degeneration, rheumatoid arthritis, and psoriasis.

A suitable dosage of the inventive antibodies and compositions (e.g., pharmaceutical compositions) depends on many factors, such as formulation methods, administration methods, ages of patients, body weight, gender, pathologic conditions, diets, administration time, administration route, excretion speed, and reaction sensitivity. The desirable dose of the pharmaceutical composition may be in the range of about 0.001 to 100 mg/kg (e.g., about 0.005 mg/kg, about 0.01 mg/kg, about 0.05 mg/kg, about 0.1 mg/kg, about 0.5 mg/kg, about 1 mg/kg, about 5 mg/kg, about 10 mg/kg, or about 50 mg/kg) for an adult. The term "pharmaceutically effective amount" used herein refers to a sufficient amount used in preventing or treating cancer and/or angiogenesis-related diseases.

The inventive antibodies and compositions can be formulated (e.g., with a pharmaceutically acceptable carrier and/or an additive) into a unit or a multiple dosage form by a well-known method in the art. In this regard, the formulation can be a solution in oil or an aqueous medium, a suspension, a syrup, an emulsifying solution, an extract, powder, granules, a tablet, or a capsule, and may further include a dispersing or a stabilizing agent. In addition, the inventive antibodies and compositions can be administered as an individual drug, or together with other drugs, and can be administered sequentially or simultaneously with pre-existing drugs.

The inventive antibodies and compositions also can be formulated as an immunoliposome. The liposome containing the antibody can be prepared using a well-known method in the art. For example, the immunoliposome is a lipid composition including phosphatidylcholine, cholesterol, and polyethyleneglycol-derived phosphatidylethanolamine, and can be prepared by a reverse phase evaporation method. For example, Fab' fragments can be adhered to the liposome through thiol-disulfide exchange. A chemical drug, such as doxorubicin, also can be included in the liposome.

According to an embodiment of the present invention, the antibody can act as an antagonist against the c-Met protein.

The term "antagonist" as used herein includes all molecules that partially or entirely block, inhibit, and/or neutralize at least one biological activity of its target (i.e., c-Met). For example, the term "antagonist antibody" refers to an antibody that inhibits or decreases the biological activity of an antigen to which the antibody binds (e.g., c-Met). An antagonist can decrease receptor phosphorylation due to binding receptors to ligands or incapacitate or destroy cells that are activated by the ligands. Also, an antagonist can completely block interaction between a receptor and a ligand or decrease the interaction due to tertiary structure change or down regulation of the receptor.

One or more embodiments of the present invention will now be described in further detail with reference to the following Examples. However, these examples are for the illustrative purposes only and are not intended to limit the scope of the invention.

EXAMPLE 1

This example demonstrates the preparation of a mouse antibody (AbF46) against c-Met.

(1) Immunization of Mice.

To obtain immunized mice for developing hybridoma cell lines, 100 μg of human c-Met/Fc fusion protein (R&D Systems, Minneapolis, Minn., USA) and a complete Freund's adjuvant were mixed. The mixture was administered via an intraperitoneal injection to each of five 4- to 6-week-old BALB/c mice (Japan SLC, Inc., Hamamatsu, Japan).

Two weeks later, the antigen (half the previously injected amount) was mixed with an incomplete Freund's adjuvant using the same method as described above. This mixture was administered to each mouse via an intraperitoneal injection.

One week later, final boosting was performed with 50 μg of c-Met/Fc fusion protein and complete Freund's adjuvant. Blood was collected from the tail of each mouse after three days to obtain serum. Then, serum was diluted at 1/1000 with PBS, and an enzyme-linked immunosorbent assay (ELISA) was performed to analyze whether the titer of the antibody recognizing c-Met increased as compared to ELISA before boosting. Afterwards, mice in which a sufficient amount of the antibody was obtained were selected, and a cell fusion process was performed on the selected mice.

(2) Cell Fusion and Preparation of the Hybridoma Cells.

Three days before a cell fusion experiment, a mixture of PBS and 50 μg of human c-Met/Fc fusion protein was administered via an intraperitoneal injection to each mouse. Each immunized mouse was anesthetized, and its spleen located on the left side of the body was then extracted and ground with a mesh to isolate cells, which were mixed with a culture medium (DMEM) to prepare a spleen cell suspension. The suspension was centrifuged to collect a cell layer. The obtained $1 \times 10^8$ spleen cells were mixed with $1 \times 10^8$ myeloma cells (Sp2/0), and the mixture was centrifuged to precipitate the cells. The precipitate was slowly dispersed, treated with 1 ml of 45% polyethylene glycol (PEG) in DMEM, and maintained at 37° C. for one minute before adding 1 ml of DMEM. After introducing additional 10 ml of DMEM for 1 minute, the resulting suspension was maintained in a water bath at 37° C. for 5 minutes. The total amount thereof was made to reach 50 ml by addition of DMEM, and the resulting suspension was centrifuged. The resulting cell precipitate was re-suspended in an isolation medium (HAT medium) at a concentration of $1-2 \times 10^5$ cells/ml. Then, the resultant suspension was distributed to a 96-well plate (0.1 ml per well), which was placed in a carbon dioxide incubator at 37° C. to prepare the hybridoma cells.

(3) Selection of the Hybridoma Cells that Produce Monoclonal Antibodies Against the c-Met Protein.

To select the hybridoma cells that specifically bind to c-Met from the hybridoma cells prepared in (2), ELISA was performed to screen for the cells that produced antibodies active against human c-Met/Fc fusion protein and human Fc protein.

50 μl (2 μg/ml) of human c-Met/Fc fusion protein was coated on each well of a microtiter plate, and unreacted antigens were removed by washing. To exclude antibodies binding to Fc, but not to c-Met, the human Fc protein was coated on each well of a different microtiter plate using the same method as above. Next, 50 μl of a hybridoma cell suspension was added to each well of the microtiter plates to react for 1 hour. Then, the microwell plates were washed with a phosphate buffer-tween 20 (TBST) solution. Goat anti-mouse IgG-horseradish peroxidase (IgG-HRP) was added thereto, and a reaction was allowed to occur at room temperature for 1 hour, and washing was performed with the TBST solution to remove unreacted antibodies.

Subsequently, substrate solution (OPD) of peroxidase was added to each well, and the reaction degree was evaluated by measuring the absorption at 450 nm using an ELISA reader. Through this method, hybridoma cell lines that produce antibodies highly specific to the human c-Met protein and not to the human Fc protein were repeatedly selected. A limiting dilution was performed on the obtained hybridoma cell lines to obtain a single clone of hybridoma cell lines producing monoclonal antibodies. The selected hybridoma cell line producing the monoclonal antibody was registered in the Korean Cell Line Bank with accession number KCLRF-BP-00220 on Oct. 9, 2009.

(4) Production and Purification of the Monoclonal Antibody.

The hybridoma cells obtained in (3) above were cultured in a serum-free medium to produce and purify the monoclonal antibodies.

First, the hybridoma cells cultured in 50 ml of culture medium (DMEM) with 10% FBS were centrifuged to obtain a cell precipitate, which was washed with 20 ml of PBS more than twice to remove the FBS. Then, 50 ml of DMEM was introduced to re-suspend the cell precipitate, and the resulting suspension was incubated in a carbon dioxide incubator at 37° C. for 3 days. After centrifugation to remove antibody-producing cells, cell culture including antibodies was isolated and stored at 4° C., or used directly. Antibodies were purified from 50 to 300 ml of the culture using a AKTA purification device (GE Healthcare Life Sciences, Piscataway, N.J., USA) equipped with an affinity column (protein G agarose column; Phizer, New York, N.Y., USA), and the purified antibodies were stored by replacing the supernatant with PBS using a filter for protein aggregation (Amicon-Millipore, Billerica, Mass., USA).

EXAMPLE 2

This example demonstrates the preparation of a chimeric antibody (chAbF46) against c-Met.

Generally, when a mouse antibody is injected into a human for medical purposes, immunogenicity often can occur. Thus, to reduce such a response, a chimeric antibody (chAbF46), in which a constant region (except variable regions involved in binding of antigens) is substituted with sequences of a human IgG1 antibody, was prepared from the mouse antibody AbF46 prepared in Example 1.

Polynucleotides were synthesized to have a structure of each designed with EcoRI-signal sequence-VH-NheI-CH-TGA-XhoI (SEQ ID NO: 7) as a sequence corresponding to a heavy chain and EcoRI-signal sequence-VL-BsiWI-CL-TGA-XhoI (SEQ ID NO: 8) as a sequence corresponding to a light chain. Then, vectors for expression of a chimeric antibody were constructed by cloning a DNA fragment (SEQ ID NO: 7) having the sequence corresponding to a heavy chain into pOptiVEC™-TOPO TA Cloning Kit included in Opti-CHO™ Antibody Express Kit (Invitrogen, Grand Island, N.Y., USA; Cat. no. 12762-019) and a DNA fragment (SEQ ID NO: 8) having the sequence corresponding to a light chain into pcDNA™3.3-TOPO TA Cloning Kit (Invitrogen; Cat. no. 8300-01) by using a restriction enzyme, EcoRI (New England Biolabs, Ipswich, Mass., USA; Cat. No. R0101S) and XhoI (New England Biolabs; Cat. No. R0146S), respectively.

The constructed vectors were amplified using a Qiagen Maxiprep kit (Qiagen, Valencia, Calif., USA: Cat. no. 12662), and vectors including the heavy chain and vectors including the light chain were added to 293T cells ($2.5 \times 10^7$) at a ratio of about 4:1 (about 80 μg:20 μg) with 360 μl of 2 M $CaCl_2$ and were transfected. Next, the mixture was cultured in a DMEM medium added with 10% FBS at 37° C. under 5% $CO_2$ conditions for 5 hours, and then cultured in a DMEM medium without FBS at 37° C. under 5% $CO_2$ conditions for 48 hours.

Each 100 ml of supernatant was obtained by centrifuging the cultured cells and was purified using AKTA Prime (GE Healthcare Life Sciences). Protein A column (GE Healthcare Life Sciences, Cat. no. 17-0405-03) was placed in AKTA Prime, and the cultured solution was made to flow at a flow rate of 5 ml/min and was eluted with IgG elution buffer (Thermo Scientific, Hudson, N.H., USA, Cat. no. 21004). The buffer was replaced with a PBS buffer, and thus a final chimeric antibody (hereinafter, chAbF46) was purified.

EXAMPLE 3

This examples demostrates the preparation of a humanized antibody (huAbF46) from a chimeric antibody.

(1) Heavy Chain Humanization.

For 2 types of designs of H1-heavy and H3-heavy, a human germline gene which is most homologous to a VH gene of a mouse antibody AbF46 was first analyzed using Ig Blast (National Center for Biotechnology Information, National Institutes of Health, U.S. National Library of Medicine, Bethesda Md.). As a result, VH3-71 having 83% identity at the amino acid level to a VH gene of mouse antibody AbF46 was confirmed. CDR-H1, CDR-H2, and CDR-H3 of the mouse antibody AbF46 were numbered using Kabat numbering and designed so that a CDR portion of the mouse antibody AbF46 was introduced in a framework of VH3-71. Amino acids of No. 30 (S→T), No. 48 (V→L), No. 73 (D→N), and No. 78 (T→L) were back-mutated to an amino acid sequence of an original mouse AbF46 antibody. Then, in the H1-heavy, the amino acids of No. 83 (R→K) and No. 84 (A→T) were additionally mutated, thereby completing construction of H1-heavy (SEQ ID NO: 9) and H3-heavy (SEQ ID NO: 10).

For a design of H4-heavy (SEQ ID NO: 11), a framework sequence of a human antibody was obtained, and VH3 subtype known as having a sequence similar to a mouse framework sequence of AbF46 antibody and conventionally known as being most stable was used to introduce CDR-H1, CDR-H2, and CDR-H3 of mouse antibody AbF46 defined as Kabat numbering.

(2) Light Chain Humanization.

For 2 types of designs of H1-light (SEQ ID NO: 12) and H2-light (SEQ ID NO: 13), a human germline gene which is most homologous to a VL gene of a mouse antibody AbF46 was analyzed using Ig Blast (National Center for Biotechnology Information, National Institutes of Health, U.S. National Library of Medicine, Bethesda Md.) As a result, VK4-1 having a 75% identity at the amino acid level to a VL gene of mouse antibody AbF46 was confirmed. CDR-L1, CDR-L2, and CDR-L3 of the mouse antibody AbF46 were numbered using Kabat numbering and designed so that the CDR portion of the mouse antibody AbF46 was introduced in a framework of VK4-1. In the H1-light, 3 amino acids of No. 36 (Y→H), No. 46 (L→M), and No. 49 (Y→I) were back-mutated, and, in the H2-light, only one amino acid of No. 49 (Y→I) was back-mutated.

For a design of H3-light (SEQ ID NO: 14), a human germline gene which is most homologous to a VL gene of a mouse antibody AbF46 was analyzed using Ig Blast (National Center for Biotechnology Information, National Institutes of Health, U.S. National Library of Medicine, Bethesda Md.). As a result, VK2-40 and VK4-1 mentioned above were chosen. Mouse antibodies AbF46 VL and VK2-40 having 61% identity at an amino acid level to a VL gene of mouse antibody AbF46 were confirmed. CDR-L1, CDR-L2, and CDR-L3 of the mouse antibody AbF46 were numbered using Kabat numbering and designed so that the CDR portion of the mouse antibody AbF46 was introduced in a framework of VK4-1. H3-light back-mutated 3 amino acids of No. 36 (Y→H), No. 46 (L→M), and No. 49 (Y→I).

For a design of H4-light (SEQ ID NO: 15), a framework sequence of a human antibody was obtained, and Vk1 subtype conventionally known as being most stable was used to introduce CDR-L1, CDR-L2, and CDR-L3 of mouse antibody AbF46 numbered using Kabat numbering. In the H4-light, 3 amino acids of No. 36 (Y→H), No. 46 (L→M), and No. 49 (Y→I) were additionally back-mutated.

Then, vectors for expression of the humanized antibody were constructed by cloning DNA fragments (H1-heavy; SEQ ID NO: 16, H3-heavy; SEQ ID NO: 17, and H4-heavy; SEQ ID NO: 18) having the sequence corresponding to a heavy chain into pOptiVEC™-TOPO TA Cloning Kit included in OptiCHO™ Antibody Express Kit (Invitrogen; Cat. no. 12762-019) and DNA fragments (H1-light; SEQ ID NO: 19, H2-light; SEQ ID NO: 20, H3-light; SEQ ID NO: 21, and H4-light; SEQ ID NO: 22) having the sequence corresponding to a light chain into pcDNA™3.3-TOPO TA Cloning Kit (Invitrogen; Cat. no. 8300-01) by using a restriction enzyme, EcoRI (New England Biolabs; Cat. no. R0101S) and XhoI (New England Biolabs; Cat. no. R0146S), respectively.

The constructed vectors were amplified using Qiagen Maxiprep kit (Qiagen; Cat. no. 12662). Vectors including the heavy chain and vectors including the light chain were added to 293T cells ($2.5 \times 10^7$) at a ratio of about 4:1 (about 80 μg:20 μg) with 360 μl of 2 M $CaCl_2$ and were transfected. Next, the mixture was cultured in a DMEM medium added with 10% FBS at 37° C. under 5% $CO_2$ conditions for 5 hours, and then cultured in a DMEM medium without FBS at 37° C. under 5% $CO_2$ conditions for 48 hours.

Each 100 ml of supernatants was obtained by centrifuging the cultured cells and was purified using AKTA Prime (GE Healthcare Life Sciences). Protein A column (GE Healthcare Life Sciences; Cat. no. 17-0405-03) was placed in AKTA Prime, and the cultured solution was made to flow at a flow rate of 5 ml/min and was eluted with IgG elution buffer (Thermo Scientific; Cat. no. 21004). The buffer was exchanged with a PBS buffer, and thus a final humanized antibody (hereinafter, huAbF46) was purified.

EXAMPLE 4

This example demonstrates the preparation of a chimeric antibody and humanized antibody with a modified hinge region.

A hinge of human IgG1 had an amino acid sequence of EPKSCDKTHTCPPCP (SEQ ID NO: 23). The hinge was replaced with either (a) a U7-HC6 hinge having an amino acid sequence of SEQ ID NO: 5, (b) a U3-HC9 hinge having an amino acid sequence of SEQ ID NO: 24, (c) a U6-HC8 hinge having an amino acid sequence of SEQ ID NO: 25, (d) a U6-HC7 hinge having an amino acid sequence of SEQ ID NO: 6, and (e) a U8-HC5 hinge having an amino acid sequence of SEQ ID NO: 26. For the replacement, polynucleotides (SEQ ID NO: 27 through SEQ ID NO: 31, respectively) for each hinge sequence were synthesized (Bioneer, Inc., Alameda, Calif., USA). The synthesized polynucleotides were cloned into a vector comprising the heavy chain region of chAbF46 antibody or huAbF46 antibody prepared in Examples 2 or 3 by using restriction enzymes, KasI (New England Biolabs; Cat. no. R0544S) and BsrGI (New England Biolabs; Cat. no. R0575S).

Vectors comprising a heavy chain region having a modified hinge region and vectors comprising a light chain region of chAbF46 or huAbF46 were each amplified using Qiagen Maxiprep kit (Qiagen; Cat. no. 12662), and the vectors comprising the heavy chain and vectors comprising the light chain were added to 293T cells ($2.5 \times 10^7$) at a ratio of about 4:1 (about 80 µg: 20 µg) with 360 µl of 2 M $CaCl_2$ and were transfected. Next, the mixture was cultured in a DMEM medium added with 10% FBS at 37° C. under 5% $CO_2$ conditions for 5 hours, and then cultured in a DMEM medium without FBS at 37° C. under 5% $CO_2$ conditions for 48 hours.

Each 100 ml of supernatants was obtained by centrifuging the cultured cells and was purified using AKTA Prime (GE Heathcare Life Sciences). Protein A column (GE Heathcare Life Sciences; Cat. no. 17-0405-03) was placed in AKTA Prime, and the cultured solution was made to flow at a flow rate of 5 ml/min and was eluted with IgG elution buffer (Thermo Scientific; Cat. no. 21004). The buffer was exchanged with a PBS buffer, and thus finally a chimeric antibody with a modified hinge region and a humanized antibody with a modified hinge region (hereinafter, expressed with a hinge name after chAbF46 or huAbF46) was purified.

EXAMPLE 5

This example demonstrates the reactivity to c-Met of the chAbF46 antibody and huAbF46 antibody.

An ELISA was used to analyze whether the chAbF46 antibody and the huAbF46 antibody that were prepared in Examples 2 and 3 recognized the murine c-Met antigen. The humanized antibody used in the current embodiment was of 4 types and each of the heavy chain and the light chain combination is as shown in Table 1.

TABLE 1

|  | H1-light | H2-light | H3-light | H4-light |
|---|---|---|---|---|
| H1-heavy | huAbF46-H1 | huAbF46-H2 | — | — |
| H3-heavy | — | — | huAbF46-H3 | — |
| H4-heavy | — | — | — | huAbF46-H4 |

First, 50 µl of human c-Met proteins (R&D Systems) at a concentration of 2 µg/ml were added to separate wells of a microtiter plate, and uncoated antigens were removed by washing. Next, 50 ng of the purified antibody was added to each well and allowed to react for 1 hour. Then, washing was performed with a phosphate buffer-tween 20 (TBST) solution. Goat anti-mouse IgG-HRP was added thereto and allowed to react at room temperature for 1 hour, and the wells were washed with the TBST solution.

Afterwards, a substrate solution (OPD) of peroxidase was introduced to each well, and the reaction degree was evaluated by measuring the absorption at 450 nm using an ELISA reader to determine whether huAbF46 or chAbF46 were bound to the human c-Met protein.

As shown in FIG. 1, the chimeric antibody chAbF46 and the humanized antibodies huAbF46-H1, huAbF46-H2 and huAbF46-H4 maintained an antigen-recognizing ability.

EXAMPLE 6

This example demonstrates the agonism huAbF46.

A BrdU assay was performed using Caki-1 cells (Korean Cell Line Bank) to compare the degree of agonism of 3 types of humanized antibodies (huAbF46-H1, huAbF46-H2, and huAbF46-H4) described in Example 5. A comparison was performed based on agonism of a mouse AbF46 antibody. Mouse IgG was used as a negative control, and the 5D5 antibody (ATCC Cat. no. HB11895 separated and purified from a hybridoma cell), which is well known as an agonist, was used as a positive control.

Figure 2:
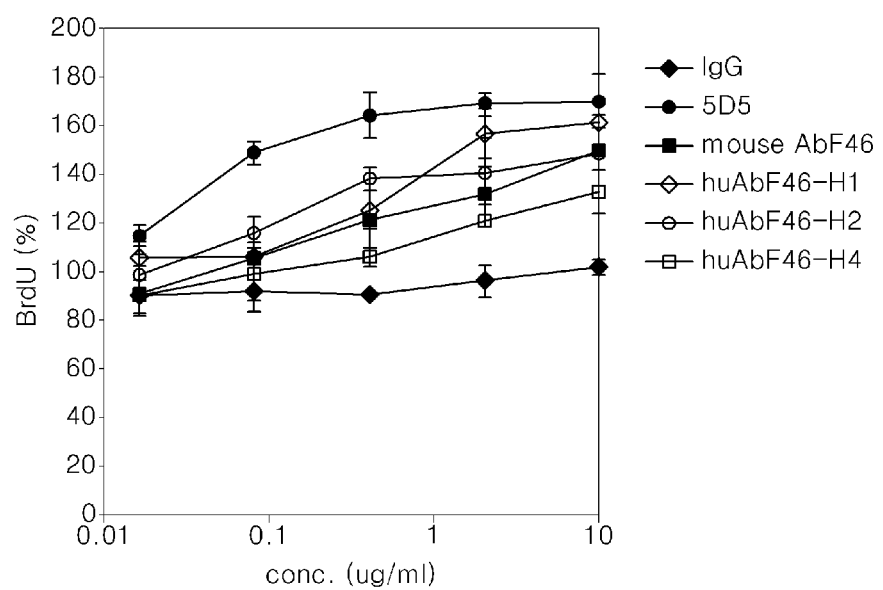
FIG. 2 is a graph illustrating the percentage of 5-bromo-2'-deoxyuridine (BrdU) incorporated into cellular DNA of NCI-H441 cells (y-axis) following in vitro administration of the inventive antibodies at particular concentrations (μg/ml) (x-axis).

As shown in FIG. 2, the agonism effects of the huAbF46 humanized antibodies increased in a concentration-dependent manner. For the huAbF46-H4 humanized antibody, agonism was generally lower than mouse antibody AbF46.

As described in Examples 5 and 6, the binding affinity to c-Met protein of the hAbF46-H1 humanized antibody and the hAbF46-H4 humanized antibody was measured using Biocare (GE Healthcare Life Sciences). Each of antibodies was immobilized to about 80~110 RU on a CM5 chip, and the c-Met protein (which is an antigen) was injected at nine different concentrations within a range of about 100 nM to about 0.39 nM at a rate of 30 µl/min to obtain $k_{on}$ and $k_{off}$ values as illustrated in Table 2. $K_D$ values were calculated from the $k_{on}$ and $k_{off}$ values.

TABLE 2

| Antibody | $k_{on}$ (1/Ms) | $k_{off}$ (1/s) | $K_D$ (nM) |
|---|---|---|---|
| chAbF46 | $3.63 \times 10^5$ | $3.67 \times 10^{-4}$ | 1.01~1.42 |
| huAbF46-H1 | $3.46 \times 10^5$ | $6.55 \times 10^{-4}$ | 1.89~1.97 |
| huAbF46-H4 | $3.39 \times 10^5$ | $6.96 \times 10^{-4}$ | 2.05~2.39 |

The chimeric antibody, chAbF46, showed about 1.01 to about 1.42 nM of binding affinity to c-Met protein, and the 2 types of humanized antibodies (hAbF46-H1 and hAbF46-H4) showed about 1.89 nM to about 1.97 nM and about 2.05 to about 2.39 nM of binding affinity (see Table 2). Therefore, it was confirmed that the 2 types of humanized antibodies maintained a binding affinity to c-Met protein similar to that of the chimeric antibody.

EXAMPLE 7

This example demonstrates the analysis of the affinity to c-Met protein of chAbF46 antibody with modified hinge region.

A binding affinity to c-Met protein of each of the chimeric antibody chAbF46 and the chimeric antibody chAbF46 with a modified hinge region prepared in Examples 2 and 4 was measured using Biocare (GE Healthcare Life Sciences). Each of antibodies was immobilized to about 80-110 RU on a CM5 chip, and the c-Met protein was injected at nine different concentrations within a range of about 100 nM to about 0.39 nM at a rate of 30 μl/min to obtain $k_{on}$ and $k_{off}$ values as illustrated in Table 3. $K_D$ values were calculated from the $k_{on}$ and $k_{off}$ values.

TABLE 3

| Antibody | $k_{on}$ (1/Ms) | $k_{off}$ (1/s) | $K_D$ (nM) |
|---|---|---|---|
| chAbF46 | $3.63 \times 10^5$ | $3.67 \times 10^{-4}$ | 1.01 |
| chAbF46-U6-MC7 | $4.03 \times 10^5$ | $6.06 \times 10^{-4}$ | 1.51 |
| chAbF46-U3-HC9 | $4.00 \times 10^5$ | $5.54 \times 10^{-4}$ | 1.38 |
| chAbF46-U6-HC8 | $4.69 \times 10^5$ | $6.26 \times 10^{-4}$ | 1.34 |
| chAbF46-U6-HC7 | $3.76 \times 10^5$ | $6.14 \times 10^{-4}$ | 1.63 |
| chAbF46-U8-HC5 | $5.15 \times 10^5$ | $6.78 \times 10^{-4}$ | 1.32 |
| chAbF46-U7-HC6 | $5.18 \times 10^5$ | $8.62 \times 10^{-4}$ | 1.66 |

The chimeric antibody, chAbF46, showed about 1.01 of binding affinity to c-Met protein, and the 5 chimeric antibodies with a modified hinge region showed about 1.34 nM to about 1.66 nM (Table 3) of binding affinity. Therefore, it was confirmed that the chimeric antibodies with modified hinge region maintained a binding affinity without reduction in binding affinity to c-Met protein similar to that of the chimeric antibody chAbF46.

EXAMPLE 8

This example demonstrates the agonism of chAbF46 antibody with modified hinge region using a BrdU assay.

To compare a degree of agonism of a humanized antibody with the modified hinge region prepared in Example 4, a BrdU assay using NCI-H441 cells was performed. NCI-H441 (human lung cancer) cells were suspended in a RPMI 1640 medium (Gibco/Invitrogen; Grand Island, N.Y., USA) ($2 \times 10^5$ cells/ml), and about 100 μl of the suspension was introduced to each well of a 96-well tissue culture plate (Corning, Lowell, Mass., USA).

The suspension was incubated at 37° C. under 5% $CO_2$ conditions for 24 hours. Then, the medium was completely removed and replaced with RPMI 1640 diluted with the antibody. After incubating the suspension at 37° C. under 5% $CO_2$ conditions for 21 hours, 5-bromo-2'-deoxyuridine (BrdU) was added and the BrdU assay (Roche, Indianapolis, Ind., USA) was performed after a further 3 hours of incubation. After denaturating/fixing cells on the plate, an anti-BrdU antibody was added and a matrix was added after an hour to measure a color reaction using an ELISA spectraMax reader (Molecular Devices, Sunnyvale, Calif., USA) at 370 nm. A comparison was performed based on agonism of a mouse AbF46 antibody. Mouse IgG was used as a negative control, and the 5D5 antibody (well known as an agonist) was used as a positive control.

Figure 3:
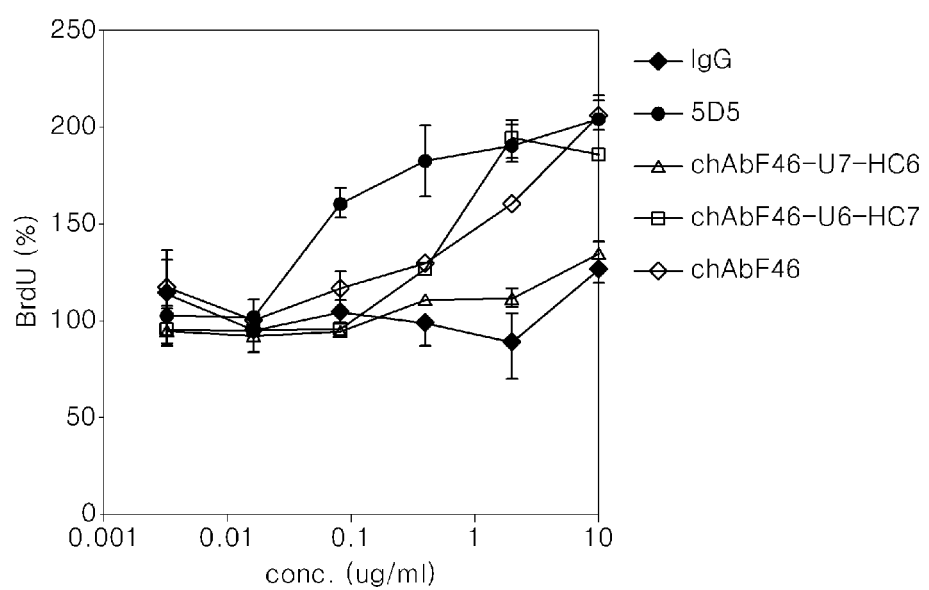
FIG. 3 is a graph illustrating the percentage of 5-bromo-2'-deoxyuridine (BrdU) incorporated into cellular DNA of NCI-H441 cells (y-axis) following in vitro administration of the inventive antibodies at particular concentrations (μg/ml) (x-axis).

As shown in FIG. 3, the chimeric antibody chAbF46 (chAbF46-U7-HC6 or chAbF46-U6-HC7) with a hinge region modified to U7-HC6 or U6-HC7 reduces a side effect of agonism.

EXAMPLE 9

This example demonstrates the agonism of the chAbF46 antibody with modified hinge region by Akt phosphorylation.

To compare agonism of the chimeric antibody with the modified hinge region prepared in Example 4, Caki-1 cells (Korean Cell Line Bank) were used to confirm a degree of Akt protein phosphorylation which is a standard involved in low signal transduction of c-Met and cell multiplication. Mouse IgG was used as a negative control, and the 5D5 antibody (well known as an agonist) was used as a positive control.

Figure 4:
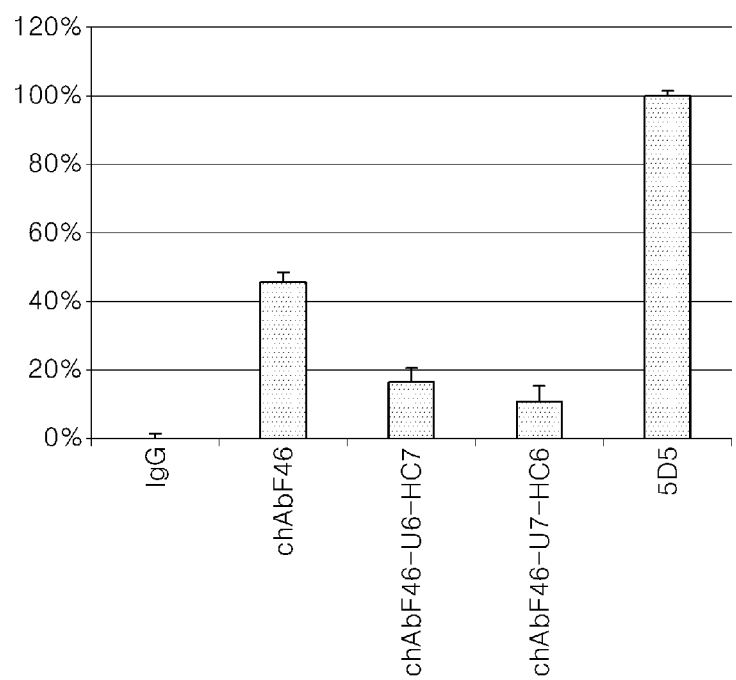
FIG. 4 is a graph illustrating the percentage of Akt phosphorylation (y-axis) in Caki-1 cells following in vitro administration of the inventive antibodies (x-axis).

Caki-1 cells ($2 \times 10^5$ cells/ml) were introduced to a 96-well plate, and after 24 hours, the antibodies set forth in FIG. 4 in serum free medium (5 μg/ml) were added to cells and cultured for 30 minutes. Lysis of the cells of treated antibodies was performed and a degree of Akt phosphorylation was measured using PathScan™ phospho-AKT1 (Ser473) chemiluminescent Sandwich ELISA kit (Cell Signaling, Danvers, Mass., USA; Cat. no. 7134S).

As shown in FIG. 4, chimeric antibodies with a modified hinge region, chAbF46-U7-HC6 and chAbF46-U6-HC7, both showed less than 20% of degree of Akt phosphorylation, and thus, the chimeric antibodies with modified hinge region decrease agonism.

EXAMPLE 10

This example demonstrates the analysis of the anti-cancer effect of chAbF46 antibody with modified hinge region in vitro.

To confirm anti-cancer effects due to cancer cell proliferation inhibition of the chimeric antibody with modified hinge region, MKN45 gastric cancer cells (Japanese Cancer Research Bank, JCRB, Tokyo, Japan) expressing c-Met on the surfaces of the cells were used to perform in vitro cell proliferation analysis.

$1 \times 10^4$ cells suspended in 50 μl of 5% FBS/DMEM culture were introduced to each well of a 96-well plate. The cells were with a concentration of 0.01 μg/ml, 0.1 μg/ml, 1 μg/ml, or 10 μg/ml of mouse IgG, chAbF46-U7-HC6, chABF46-U6-HC7. After incubating for 72 hours, the number of cells was quantified by using CellTiter-Glo™ Luminescent Cell Viability Assay Kit (Promega, Madison, Wis., USA; Cat. no. G7570) with a leuminometer (2104 Multilabel reader from PerkinElmer, Downers Grove, Ill., USA).

Figure 5:
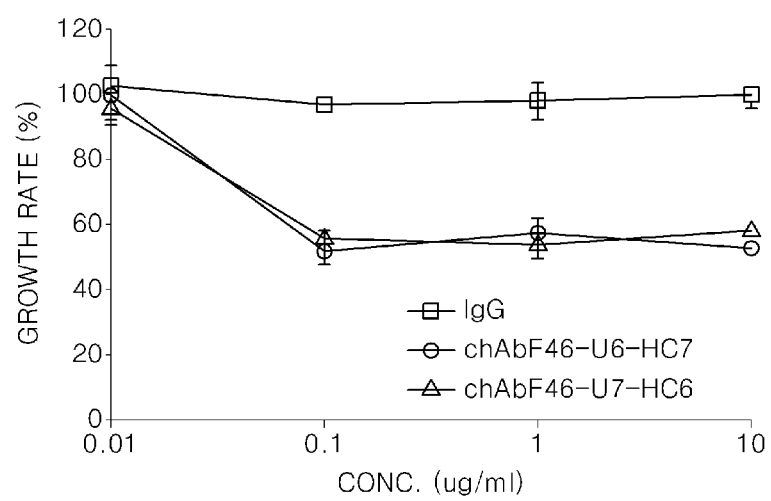
FIG. 5 is a graph illustrating the percent growth rate (y-axis) of MKN45 gastric cancer cells expressing c-Met following in vitro administration of the inventive antibodies at particular concentrations (μg/ml) (x-axis).

As shown in FIG. 5, while mouse IgG u (negative control) does not inhibit cancer cell proliferation, chAbF46-U7-HC6 and chAbF46-U6-HC7 resulted in a decreased growth rate illustrating cancer cell proliferation inhibition.

EXAMPLE 11

This example demonstrates the analysis of the anti-cancer effect of chAbF46 antibody with modified hinge region in vivo.

To confirm anti-cancer effects of the chimeric antibody with the modified hinge region prepared in Example 4, the size of tumor cells in a gastric cancer mouse xenograft model transplanted with MKN45 cells (Japanese Cancer Research Bank, JCRB, Tokyo, Japan) was observed following the in vivo administration of the chimeric antibody with modified hinge region.

A 50 μl suspension of gastric cancer line MKN45 cells ($5 \times 10^6$ cells/50 μl) was administered via subcutaneous injection to 6 week-old male BALB/c nude mice (Orient Bio Corp., Seongnam, Korea). After 1 week, 12 mice contracted with cancer were randomly selected. A concentration of 10 mg/kg of chAbF46-U6-HC7 was administered via intravenous injection to these mice once a week after tumor cells were formed. As a control, concentrations of 10 mg/kg and 20 mg/kg of mouse AbF46 antibody were administered to the other mice (12 mice per group) twice a week.

Figure 6:
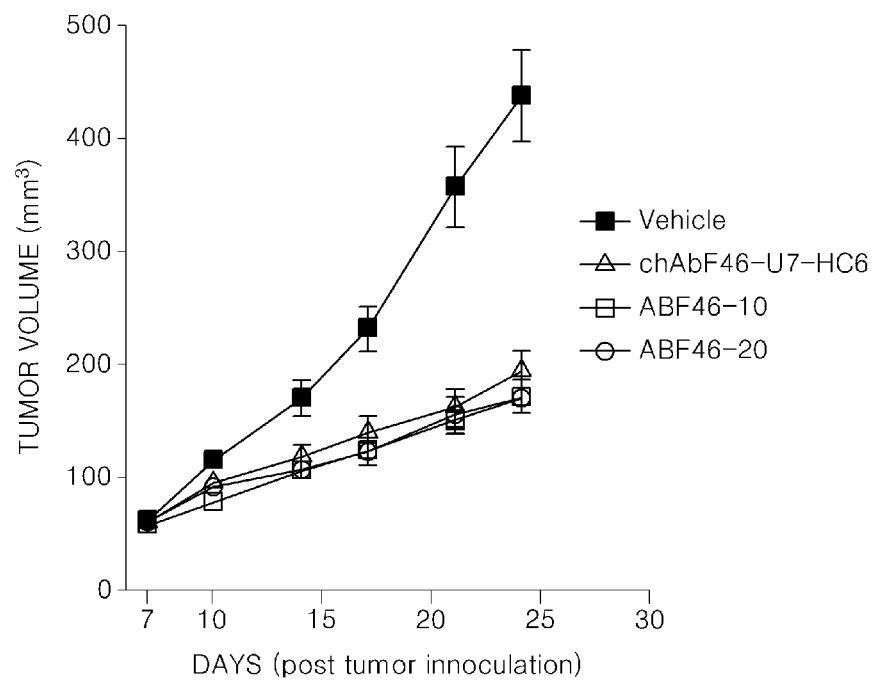
FIG. 6 is a graph illustrating the tumor volume ($mm^3$) (y-axis) on days post tumor inoculation (x-axis) in a gastric cancer mouse xenograft model, wherein the mice were administered the inventive antibodies.

As shown in FIG. 6, administrating chAbF46-U6-HC7 significantly decreased the size of the tumor cells as much as administrating the mouse AbF46 antibody, thus illustrating the inhibiting effect of cancer of the chimeric antibody.

EXAMPLE 12

This example demonstrates the analysis of affinity of huAbF46 with modified hinge region.

A binding affinity to c-Met protein of the humanized antibody huAbF46 and the humanized antibody huAbF46 with a modified hinge region prepared in Examples 3 and 4 was measured using Biocare (GE Heathcare Life Sciences). Each of antibodies shown in Table 4 was immobilized to about 80~110 RU on a CM5 chip. The c-Met protein was injected at nine different concentrations within a range of about 100 nM to about 0.39 nM at a rate of 30 μl/min to obtain $k_{on}$ and $k_{off}$ values as illustrated in Table 4. $K_D$ values were calculated from the $k_{on}$ and $k_{off}$ values.

TABLE 4

| Antibody | $k_{on}$ (1/MS) | $k_{off}$ (1/s) | $K_D$ (nM) |
| --- | --- | --- | --- |
| huAbF46-H1 | $3.46 \times 10^5$ | $6.55 \times 10^{-4}$ | 1.89 |
| huAbF46-H1-U6-MC7 | $5.16 \times 10^5$ | $10.01 \times 10^{-4}$ | 1.89 |
| huAbF46-H4 | $3.36 \times 10^5$ | $8.02 \times 10^{-4}$ | 2.39 |
| huAbF46-H4-U6-MC7 | $3.51 \times 10^5$ | $8.01 \times 10^{-4}$ | 2.28 |
| huAbF46-H4-U7-HC6 | $2.63 \times 10^5$ | $9.81 \times 10^{-4}$ | 3.74 |

The humanized antibodies huAbF46-H1 and huAbF46-H4 showed about 1.89 nM and about 2.39 nM of binding affinity to c-Met protein, and the 3 types of humanized antibodies with modified hinge regions showed about 1.89 nM to about 3.74 nM of binding affinity (Table 4). Therefore, it was confirmed that the humanized antibodies with modified hinge region maintained a binding affinity to c-Met protein similar to that of the humanized antibody huAbF46.

EXAMPLE 13

This example demonstrates the agonism of huAbF46 with modified hinge region by BrdU assay To compare the degree of agonism of a humanized antibody with the modified hinge region prepared in Example 4, a BrdU assay using NCI-H441 cells was performed. NCI-H441 (human lung cancer) cells were suspended in a RPMI 1640 medium (Gibco) ($2 \times 10^5$ cells/ml), and about 100 μl of the suspension was introduced to each well of a 96-well tissue culture plate (Corning). The suspension was incubated at 37° C. under 5% $CO_2$ conditions for 24 hours. Then, the medium was completely removed and replaced with RPMI 1640 diluted with the antibody. After incubating the suspension at 37° C. under 5% $CO_2$ conditions for 21 hours, 5-bromo-2'-deoxyuridine (BrdU) was added and the BrdU assay (Roche) was performed after a further 3 hours of incubation. After denaturating/fixing cells on the plate, an anti-BrdU antibody was added and a matrix was added after an hour to measure a color reaction using a ELISA spectraMax reader (Molecular Devices) at 370 nm. A comparison was performed based on agonism of a mouse AbF46 antibody. Mouse IgG was used as a negative control, and the 5D5 antibody (well known as an agonist) was used as a positive control.

Figure 7:
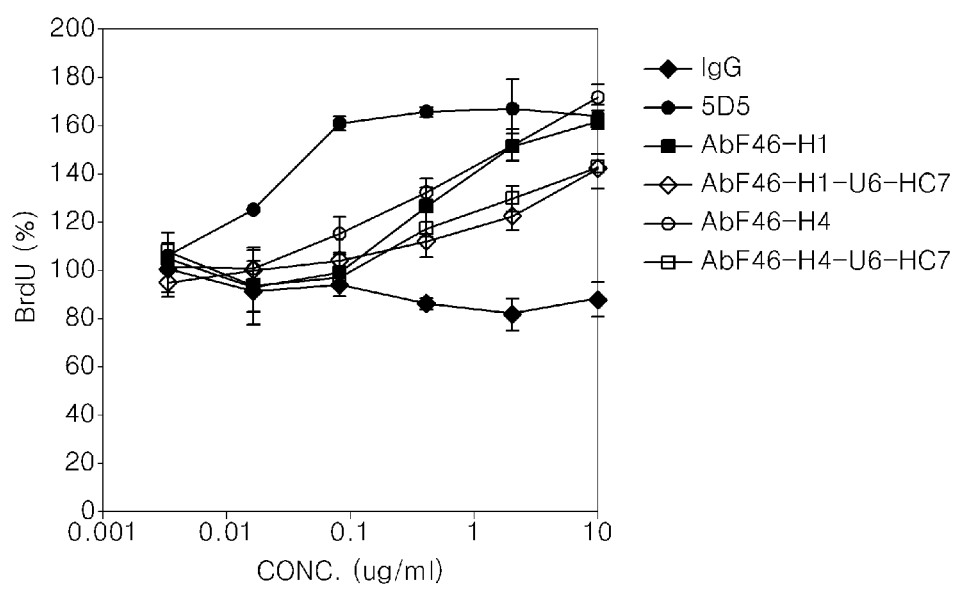
FIG. 7 is a graph illustrating the percentage of 5-bromo-2'-deoxyuridine (BrdU) incorporated into cellular DNA of NCI-H441 cells (y-axis) following in vitro administration of the inventive antibodies at particular concentrations (μg/ml) (x-axis).

As shown in FIG. 7, the 2 types of humanized antibodies (huAbF46-H1-U6-HC7 and huAbF46-H4-U6-HC7) with a hinge region modified to U6-HC7 reduced a side effect of agonism.

EXAMPLE 14

This example demonstrates the agonism of huAbF46 antibody with modified hinge region by Akt phosphorylation.

To compare agonism of the humanized antibody with the modified hinge region prepared in Example 4, Caki-1 cells (Korean Cell Line Bank) were used to confirm a degree of Akt protein phosphorylation, which is a standard involved in low signal transduction of c-Met and cell multiplication. Mouse IgG was used as a negative control, and the 5D5 antibody (well known as an agonist) was used as a positive control.

Caki-1 cells ($2 \times 10^5$ cells/ml) were introduced to a 96-well plate. After 24 hours, the antibodies set forth in FIG. 8 in a serum free medium were added to the cells and cultured for 30 minutes. Lysis of the cells of treated antibodies was performed and a degree of Akt phosphorylation was measured using PathScan™ phospho-AKT1 (Ser473) chemiluminescent Sandwich ELISA kit (Cell Signaling, Cat. no. 7134S).

Figure 8:
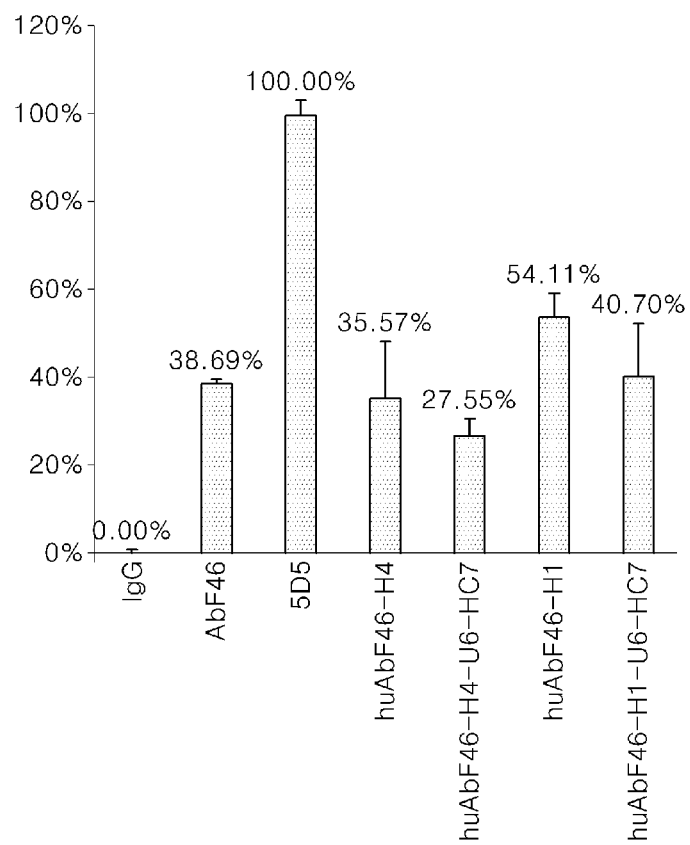
FIG. 8 is a graph illustrating the percentage of Akt phosphorylation (y-axis) in Caki-1 cells following in vitro administration of the inventive antibodies (x-axis).

As shown in FIG. 8, huAbF46-H1-U6-HC7 and huAbF46-H4-U6-HC7 both showed about a 20% decrease in degree of Akt phosphorylation compared to humanized antibodies with unmodified hinge regions (huAbF46-H1 and huAbF46-H4). Thus, the humanized antibodies with unmodified hinge region decrease the agonism.

EXAMPLE 15

This example demonstrates the analysis of an anti-cancer effect of the huAbF46 antibody with modified hinge region in vitro.

To confirm anti-cancer effects due to cancer cell proliferation inhibition of the humanized antibody with modified hinge region prepared in Example 4, MKN45 stomach cancer cells (Korean Cell Line Bank) expressing c-Met on surfaces of the cells were used to perform in vitro cell proliferation analysis.

$1 \times 10^4$ cells suspended in 50 μl of 5% FBS/DMEM culture were introduced to each well of a 96-well plate. The cells were treated with 0.01 μg/ml, 0.1 μg/ml, 1 μg/ml, or 10 μg/ml of huAbF46-H1-U6-HC7 (modified hinge), huAbF46-H4-U6-HC7 (modified hinge), huAbF46-H1, or huAbF46-H4. After incubating for 72 hours, the number of cells was quantified by using CellTiter-Glo™ Luminescent Cell Viability Assay Kit (Promega; Cat. no. G7570) with a luminometer (2104 Multilabel reader from Perkin Elmer).

Figure 9:
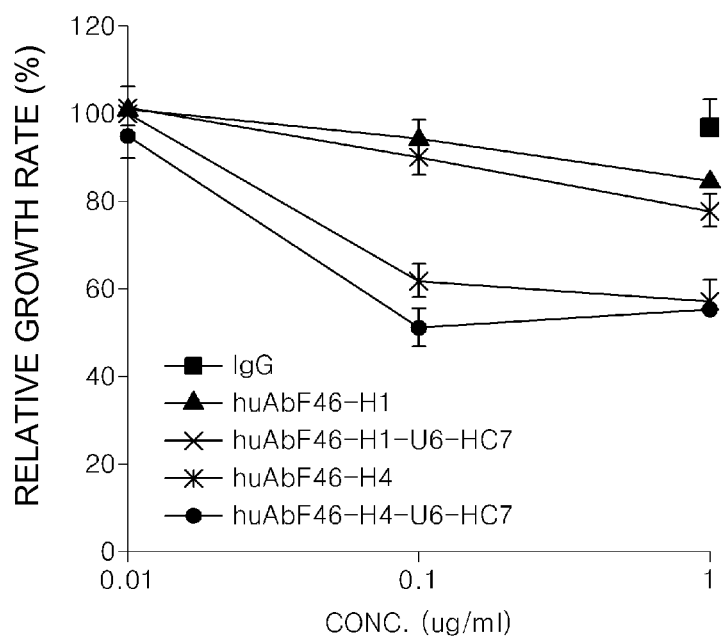
FIG. 9 is a graph illustrating the percent growth rate (y-axis) of MKN45 gastric cancer cells expressing c-Met following in vitro administration of the inventive antibodies at particular concentrations (μg/ml) (x-axis).

As shown in FIG. 9, while mouse IgG (negative control) did not inhibit cancer cell proliferation, the humanized antibodies with modified hinge regions (huAbF46-H1-U6-HC7 and huAbF46-H4-U6-HC7) and the humanized antibodies with unmodified hinge regions (huAbF46-H1 and huAbF46-H4) decreased growth rate of the cells, illustrating cancer cell proliferation inhibition. The humanized antibodies with modified hinge regions (huAbF46-H1-U6-HC7 and huAbF46-H4-U6-HC7) resulted in about 25% increased cancer cell inhibition as compared to the humanized antibodies with unmodified hinge regions (huAbF46-H1 and huAbF46-H4).

EXAMPLE 16

This example provides the CDR amino acid sequences of chimeric and humanized antibodies chAbF46 and huAbF46.

The heavy and the light chain CDR amino acid sequences of the chimeric and humanized antibody chAbF46 and huAbF46 are displayed in Table 5.

TABLE 5

| | CDR1 | CDR2 | CDR3 |
|---|---|---|---|
| AbF46 heavy chain CDR sequence | DYYMS (SEQ ID NO: 32) | FIRNKANGYT TEYSASVKG (SEQ ID NO: 33) | DNWFAY (SEQ ID NO: 34) |
| AbF46 light chain CDR sequence | KSSQSLLAS GNQNNYLA (SEQ ID NO: 35) | WASTRVS (SEQ ID NO: 36) | QQSYSAPLT (SEQ ID NO: 37) |

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated anti c-Met antibody comprising the amino acid sequences of SEQ ID NO: 1 and SEQ ID NO: 2, which correspond to the variable regions of the heavy chain and light chain of the antibody, respectively.

2. An isolated anti c-Met antibody comprising the amino acid sequences of SEQ ID NO: 3 and SEQ ID NO: 4, which correspond to the variable regions of the heavy chain and light chain of the antibody, respectively.

3. The antibody of claim 1, wherein the antibody is a monoclonal antibody.

4. The antibody of claim 1, wherein the antibody is an antigen binding fragment selected from the group consisting of scFv, (scFv)$_2$, Fab, Fab' and F(ab')$_2$.

5. The antibody of claim 1, wherein the antibody comprises a hinge region with the amino acid sequences of SEQ ID NO: 5 or SEQ ID NO: 6.

6. A composition comprising the antibody of claim 1.

7. A composition comprising the antibody of claim 2.

8. A composition comprising the antibody of claim 5.

9. A method for treating gastric cancer in a patient, the method comprising administering to the patient the composition of claim 6, thereby treating the gastric cancer.

10. A method for treating gastric cancer in a patient, the method comprising administering to the patient the composition of claim 7, thereby treating the gastric cancer.

11. A method for treating gastric cancer in a patient, the method comprising administering to the patient the composition of claim 8, thereby treating the gastric cancer.

12. The antibody of claim 2, wherein the antibody is a monoclonal antibody.

13. The antibody of claim 2, wherein the antibody is an antigen binding fragment selected from the group consisting of scFv, (scFv)$_2$, Fab, Fab' and F(ab')$_2$.

14. The antibody of claim 2, wherein the antibody comprises a hinge region with the amino acid sequences of SEQ ID NO: 5 or SEQ ID NO: 6.

15. A composition comprising the antibody of claim 14.

16. A method for treating gastric cancer in a patient, the method comprising administering to the patient the composition of claim 15, thereby treating the gastric cancer.

* * * * *